US011510926B2

(12) United States Patent
Coderre et al.

(10) Patent No.: US 11,510,926 B2
(45) Date of Patent: Nov. 29, 2022

(54) PHARMACEUTICAL SALTS/CO-CRYSTALS OF PENTOXIFYLLINE, CLONIDINE AND LINSIDOMINE WITH CAFFEIC, PROTOCATECHUIC OR ALPHA-LIPOIC ACID AN USE THEREOF FOR TREATMENT OF PAIN

(71) Applicant: THE ROYAL INSTITUTION FOR THE ADVANCEMENT OF LEARNING/MCGILL UNIVERSITY, Montréal (CA)

(72) Inventors: Terence J. Coderre, Dorval (CA); Oli Abate Fulas, Montréal (CA); André Laferrière, Montréal (CA); Ghada Ayoub, Montreal (CA); Tomislav Friščić, Verdun (CA); Dayaker Gandrath, Montréal (CA); Cristina Mottillo, St-Leonard (CA)

(73) Assignee: THE ROYAL INSTITUTION FOR THE ADVANCEMENT OF LEARNING/MCGILL UNIVERSITY, Montreal (CA)

( * ) Notice: Subject to any disclaimer, the term of this patent is extended or adjusted under 35 U.S.C. 154(b) by 192 days.

(21) Appl. No.: 17/058,161

(22) PCT Filed: May 27, 2019

(86) PCT No.: PCT/CA2019/050719
§ 371 (c)(1),
(2) Date: Nov. 24, 2020

(87) PCT Pub. No.: WO2019/227202
PCT Pub. Date: Dec. 5, 2019

(65) Prior Publication Data
US 2021/0213025 A1 Jul. 15, 2021

Related U.S. Application Data

(60) Provisional application No. 62/678,414, filed on May 31, 2018.

(51) Int. Cl.
A61K 31/5377 (2006.01)
A61K 31/4168 (2006.01)
A61K 31/522 (2006.01)
A61P 29/02 (2006.01)
A61K 9/00 (2006.01)
A61K 9/16 (2006.01)
A61K 45/06 (2006.01)

(52) U.S. Cl.
CPC ........ A61K 31/5377 (2013.01); A61K 9/0014 (2013.01); A61K 9/1682 (2013.01); A61K 31/4168 (2013.01); A61K 31/522 (2013.01); A61K 45/06 (2013.01); A61P 29/02 (2018.01)

(58) Field of Classification Search
CPC .............. A61K 31/4168; A61K 31/522; A61K 31/5377; A61K 9/0014; A61K 9/1682; A61P 25/04; A61P 29/02; C07C 59/52; C07C 65/03; C07D 233/50; C07D 271/04; C07D 339/04; C07D 473/10
See application file for complete search history.

(56) References Cited

U.S. PATENT DOCUMENTS 9,096,537 B1 8/2015 Kandula et al.

FOREIGN PATENT DOCUMENTS

CA 2796280 10/2011
WO 2010043412 A1 4/2010

OTHER PUBLICATIONS

Götz, M. et al. "Synthesis of 3-Aminosyndnone Imines". Journal of Heterocyclic Chemistry. vol. 7, No. 1. pp. 123-129, 1970.
Stepanovs, D. et al. "Cocrystals of Pentoxifylline: In Silico and Experimental Screening". Crystal Growth & Design. vol. 15, No. 8. 2015. pp. 3652-3660.
Accetto, B. "Beneficial hemorheologic therapy of chronic peripheral arterial disorders with pentoxifylline: results of double-blind study versus vasodilator-nylidrin". Am Heart J, 1982. 103(5): pp. 864-869.
Aitipamula, S. et al. "Polymorphs, Salts, and Cocrystals: What's in a Name?" Crystal Growth & Design, 2012. 12(5): pp. 2147-2152.
Areti, A. et al. "Oxidative stress and nerve damage: Role in chemotherapy induced peripheral neuropathy". Redox Biology, 2014. 2: pp. 289-295.
Bassenge, E. and W.R. Kukoveiz. "Molsidomine". Cardiovascular Drug Reviews, 1984. 2(1): pp. 177-191.
Bruehl, S. "Complex regional pain syndrome". BMJ 2015. 350: h2730 pp. 1-13.
Bussa, M. et al. "Complex regional pain syndrome type I: a comprehensive review" Acta Anaesthesiol Scand, 2015. 59(6): pp. 685-697.
Chauhan, A. & Chauhan, P. "Powder XRD Technique and its Applications in Science and Technology". Journal of Analytical & Bioanalytical Techniques, 2014. 5(5): pp. 1-5.
Coderre, T.J. et al. "Chronic post-ischemia pain (CPIP): a novel animal model of complex regional pain syndrome-Type I (CRPS-I; reflex sympathetic dystrophy) produced by prolonged hindpaw ischemia and reperfusion in the rat". Pain. 112 (2004) pp. 94-105.
Coderre, T.J. & Bennett, G.J. "A hypothesis for the Cause of Complex Regional Pain Syndrome-Type I (Reflex Sympathetic Dystrophy): Pain due to Deep-Tissue Microvascular Pathology". Pain Med. 2010. 11(8): pp. 1224-1238.

(Continued)

Primary Examiner — Sarah Pihonak
(74) Attorney, Agent, or Firm — Norton Rose Fulbright Canada LLP

(57) ABSTRACT

Disclosed are pharmaceutical salts and co-crystals of pentoxifylline, clonidine and linsidomine with caffeic acid, protocatechuic acid or α-lipoic acid, and method for preparing thereof. Also disclosed are topical compositions comprising said salts or co-crystals and use thereof for treating pain.

17 Claims, 17 Drawing Sheets

(56) References Cited

OTHER PUBLICATIONS

Coderre, T.J. "Complex regional pain syndrome—type I: what's in a name?" J Pain, 2011. 12(1): pp. 2-12.
Coderre, T.J. "Topical drug therapeutics for neuropathic pain", Expert Opinion on Pharmacotherapy, Jul. 2018, 19(11): 1211-1220.
Colloca, L. et al. "Neuropathic pain". Nature Reviews. Disease Primers. 2017. vol. 3. Article No. 17002. pp. 1-19.
Hosseini, A. and M. Abdollahi. "Diabetic Neuropathy and Oxidative Stress: Therapeutic Perspectives". Oxidative Medicine and Cellular Longevity. vol. 2013. Article ID 168039. pp. 1-15.
Kamibayashi, T. and M. Maze. "Clinical Uses of $\alpha 2$-Adrenergic Agonists". Anesthesiology. 2000. vol. 93. No. 5: pp. 1345-1349.
Khatioda, R. et al. CrystComm., 2017, 19 (46):6992-7000.
Kirchmair, R. et al. "Therapeutic Angiogenesis Inhibits or Rescues Chemotherapy-induced Peripheral Neuropathy: Taxol-and Thalidomide-induced Injury of Vasa Nervorum is Ameliorated by VEGF". Molecular Therapy. 2007. vol. 15. No. 1: pp. 69-75.
Laferriere, A. et al. "Cutaneous tactile allodynia associated with microvascular dysfunction in muscle". Molecular Pain. vol. 4. No. 49. 2008.
Lim, T.K.Y. et al. "Mitochondrial and bioenergetic dysfunction in trauma-induced painful peripheral neuropathy". Molecular pain, 2015. 11(58): pp. 1-9.
Lim, T.K.Y. et al. "Peripheral Nerve Injury Induces Persistent Vascular Dysfunction and Endoneurial Hypoxia, Contributing to the Genesis of Neuropathic Pain". The Journal of Neuroscience, 2015. 35(8): pp. 3346-3359.
Lihua, Z. et al. CrystEngComm., 2014, 16 (26):5769-5780.
Magana-Vergara, N.E. et al. Crystals (2073-4352), Mar. 2018, 8(3):130.
Mitsui, Y. et al. "Alpha-lipoic acid provides neuroprotection from ischemia-reperfusion injury of peripheral nerve". Journal of the Neurological Sciences 1999. 163. pp. 11-16.
Mittapalli, S. et al. Crystal Growth & Design, 2015, 15(5) 2493-2504.
Ragavendran, J.V. et al. "Topical Combinations Aimed at Treating Microvascular Dysfunction Reduce Allodynia in Rat Models of CRPS-I and Neuropathic Pain". J Pain. 2013. 14(1): pp. 66-78.
Ragavendran, J.V. et al. "Effects of topical combinations of clonidine and pentoxifylline on capsaicin-induced allodynia and postcapsaicin tourniquet-induced pain in healthy volunteers: a double-blind, randomized, controlled study". Pain. 2016. vol. 157. No. 10. pp. 2366-2374.
Saleh, A.M. and Rizvi, S.A.A. "Utility of Novel Dual Functionalized Cocrystallized and Ionic Liquid Based Drugs for the Pain Management". International Journal of Pharmaceutical Research and Bio-Science. vol. 5(5). 2016. pp. 97-109.
Sawynok, J. "Topical Analgesics for Neuropathic Pain in the Elderly: Current and Future Prospects". Drugs Aging, 2014 31(12): pp. 853-862.
Schreiber, A.K. et al. "Diabetic neuropathic pain: Physiopathology and treatment". World Journal of Diabetes, 2015. vol. 6. Issue 3 pp. 432-444.
Sroka, Z. and Cisowski, W. "Hydrogen peroxide scavenging, antioxidant and anti-radical activity of some phenolic acids". Food and Chemical Toxicology. 2003. vol. 41. pp. 753-758.
Stepanovs, D. & Mishnev, A. Acta Crystallographica Section C Crystal Structure Communications, 2012, 68(12): p. 488-491.
Tan, D., Loots, L., & Friscic, T. "Towards medicinal mechanochemistry: evolution of milling from pharmaceutical solid form screening to the synthesis of active pharmaceutical ingredients (APIs)". Chem. Commun. 2016. 52. pp. 7760-7781.
Thipparaboina, R., et al. "Multidrug co-crystals: towards the development of effective therapeutic hybrids". Drug Discov Today. 2016. vol. 21. No 3 pp. 481-490.
Trask, A.V. "An Overview of Pharmaceutical Cocrystals as Intellectual Property". Molecular Pharmaceutics. 2007. vol. 4. No. 3. pp. 301-309.
Wasner, G. "Vasomotor Disturbances in Complex Regional Pain Syndrome—A Review". Pain Medicine. 2010. 11: pp. 1267-1273.

PHARMACEUTICAL SALTS/CO-CRYSTALS OF PENTOXIFYLLINE, CLONIDINE AND LINSIDOMINE WITH CAFFEIC, PROTOCATECHUIC OR ALPHA-LIPOIC ACID AN USE THEREOF FOR TREATMENT OF PAIN

The present application is the 371 national phase entry of PCT/CA2019/050719 filed May 27, 2019, the content of which is hereby incorporated in its entirety. The present application also claims priority from U.S. provisional patent application Ser. No. 62/678,414, filed May 31, 2018 and entitled "PHARMACEUTICAL SALTS/CO-CRYSTALS OF PENTOXIFYLLINE, CLONIDINE AND LINSIDOMINE WITH CAFFEIC, PROTOCATECHUIC OR α-LIPOIC ACID AN USE THEREOF FOR TREATMENT OF PAIN", the disclosure of which is hereby incorporated by reference in its entirety.

FIELD OF THE DISCLOSURE

This disclosure relates to novel pharmaceutical salts and co-crystals and methods for treating pain. The present disclosure also relates to topical compositions comprising the salts/co-crystals.

BACKGROUND OF THE DISCLOSURE

Neuropathic pain and complex regional pain syndrome (CRPS) are two of the common manifestations of chronic pain. Neuropathic pain is defined as pain that results from lesion or disease of the sensory nervous system, whereas CRPS is a chronic pain condition typically of the limbs precipitated by traumatic injuries of soft tissue or bones, sometimes also including nerves.

Due to their complex multifactorial pathophysiology, the pharmacologic treatment of both conditions continues to be a challenge. For lack of better options, first line analgesics prescribed for both conditions are centrally acting anticonvulsants and antidepressants that modulate pain signalling. These drugs are sub-optimally therapeutic and have dose limiting undesirable side effects.

SUMMARY OF THE DISCLOSURE

An aspect of the disclosure relates to a compound salt/co-crystal selected from pentoxifylline caffeate, pentoxifylline protocatechuate, clonidine-α lipoate and linsidomine caffeate or a solvate thereof.

A further aspect of the disclosure relates to a composition comprising a compound salt/co-crystal as defined herein and a pharmaceutically acceptable diluent or carrier.

Still a further aspect of the disclosure relates to a method for preventing or treating pain comprising topically administering an effective amount of a salt/co-crystal or composition as defined herein to a subject in need thereof.

An aspect of the disclosure relates to a method for preparing pentoxifylline caffeate, pentoxifylline protocatechuate, clonidine α-lipoate and linsidomine caffeate salt/co-crystal or a solvate thereof, comprising liquid-assisted grinding of equimolar quantities of pentoxifylline with caffeic acid, pentoxifylline with protocatechuic acid, clonidine with α-lipoic acid or a caffeate salt with a linsidomine salt.

BRIEF DESCRIPTION OF THE DRAWINGS

Having thus generally described the nature of the invention, reference will now be made to the accompanying drawings, showing by way of illustration, an embodiment or embodiments thereof, and in which.

DETAILED DESCRIPTION

Figure 1:
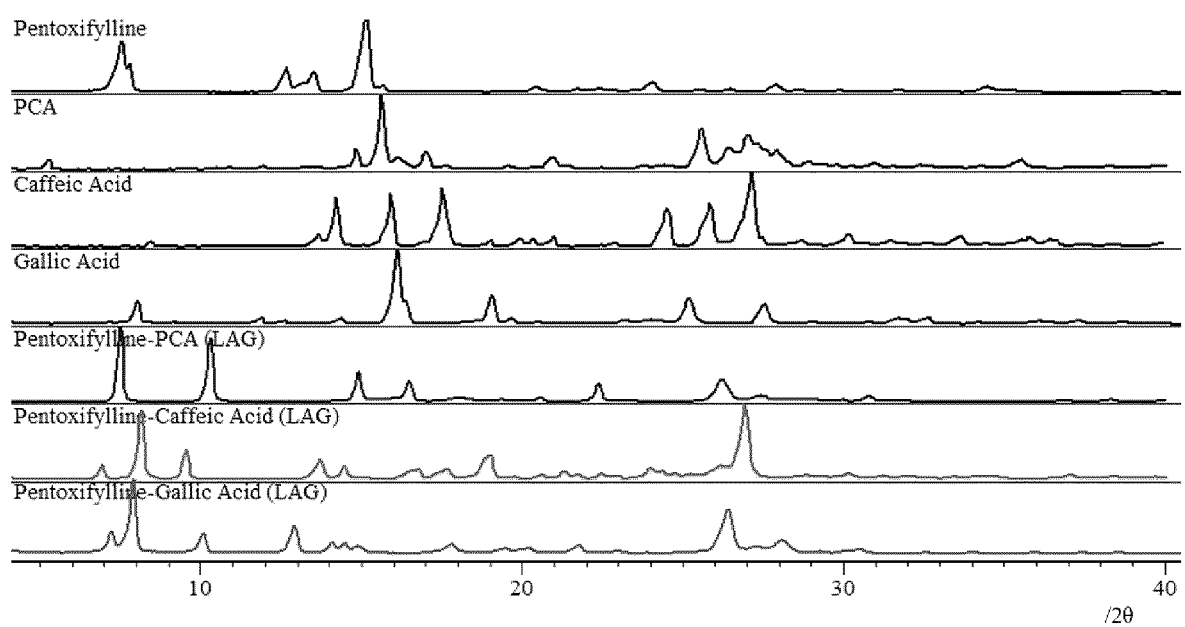
FIG. 1 is PXRD traces of pentoxifylline, certain acids (caffeic, gallic, protocatechuic (PCA)) and various co-crystals obtained after liquid-assisted grinding (LAG)

There are provided herein novel pharmaceutical salt and co-crystal compositions containing same and methods for treating pain.

This disclosure describes the synthesis and topical analgesic use of novel salts/co-crystals of pentoxifylline, clonidine and linsidomine with gallic acid, caffeic acid, protocatechuic acid and α-lipoic acid.

The incorporation of these drug groups into novel salts/co-crystals as opposed to their use as plain mixtures comes with advantages. Firstly, with their multiple components in a fixed stoichiometric ratio, salts and co-crystals exist as one compact solid form that can be dosed and studied as a single agent. This avoids the multiplied expense and extended time and effort consumed by the investigation of individual constituent drugs as in simple drug mixtures. Secondly, the formation of a salt or co-crystal has the potential to improve the physiochemical properties of constituting active pharmaceutical ingredient (API) such as the enhancement of drug stability, absorption, distribution and half-life.

Moreover, the novel salts and co-crystals described herein are synthesized using mechano-chemical techniques. Other than being a relatively gentle chemical procedure that preserves the individual drugs' integrity, it is a highly efficient, easily reproducible procedure that additionally avoids the use of bulk solvents and resulting hazardous waste, allowing for the implementation of alternatively desirable Green Chemistry.

Clonidine is an α2-adrenergic agonist with peripheral sympatholytic activity that results in vasodilation via its inhibition of norepinephrine release at the sympathetic postganglionic neuron.

Pentoxifylline is a nonselective phosphodiesterase-4 inhibitor which induces c-AMP and c-GMP accumulation in vascular smooth muscle cells bringing about vasodilation. It also improves capillary flow and increases tissue oxygenation by increasing red blood cell flexibility and reducing platelet aggregation.

Linsidomine, like pentoxifylline and clonidine, is also a vasodilator drug that acts by stimulating intracellular soluble guanylate cyclase, which results in relaxation of the vascular smooth muscle and inhibition of platelet aggregation.

Protocatechuic, gallic, and caffeic acids are all plant derived phenolic acids. α-lipoic acid is an endogenously synthesized drug that serves as a co-factor in the mitochondrial dehydrogenase complexes.

This disclosure provides the synthesis of novel drug salts/co-crystals that have superior topical analgesic efficacy and potency as compared to their parent drugs.

Mechano-Chemical Synthesis of Salts/Co-crystals

To synthesize the salts/co-crystals as defined herein, each of clonidine, pentoxifylline and linsidomine were mixed with equimolar quantities of α-lipoic acid, caffeic acid, gallic acid or protocatechuic acid as required. The mechano-chemical reactions can be run with a sufficient volume of a liquid additive (such as ethanol, nitromethane, or other liquids). The reactions can be conducted using an electrical ball mill, in a jar (such as stainless steel or PTFE or zirconia jars) together with appropriate grinding balls (such as stainless steel or PTFE or zirconia balls) while applying a grinding (milling) frequency.

Methods of Treatment and Medical Uses

One aspect of the disclosure provides a method for preventing or treating pain comprising topically administering an effective amount of a salt or co-crystal form thereof or composition as defined herein to a subject in need thereof.

In an embodiment, there is provided a method of preventing or treating pain comprising topically administering an effective amount of a salt, or co-crystal form thereof or composition as defined herein and an effective amount of at least another agent to a subject in need thereof.

In an embodiment, the salt or co-crystal form thereof or composition as defined herein and another agent may be administered concurrently or sequentially.

In an embodiment, the pain is neuropathic, ischemic or muscle pain. In other embodiments, the pain may be associated with peripheral nerve injury induced either by trauma (including post-surgical neuropathic pain and complex regional pain syndrome), metabolic dysfunction (e.g., diabetic neuropathy), chemotherapy (e.g., cancer- or HIV-chemotherapy-induced neuropathy), viral or bacterial disease (e.g., post-herpetic neuralgia), nerve compression (e.g., carpal tunnel syndrome, sciatica) or neurologic conditions (e.g., multiple sclerosis), as well as angina, peripheral arterial disease, fibromyalgia, or various conditions which may involve mixed inflammatory and neuropathic pain, such as arthritis and chronic low back pain.

As used herein the terms "topical" or "topically" refer to delivery of a drug by passage into and through the skin or mucosal tissue.

The term "effective amount" refers to an amount of a the salt/co-crystal or composition (including hydrates), which is sufficient to produce the desired result or has the desired biological effect on the treated subject. For example, an effective amount may be an amount, which at least partly alleviates, reduces, prevents or treats pain in a subject.

Pharmaceutical Compositions

In accordance with one embodiment, there are provided pharmaceutical compositions, in particular topical compositions.

The composition described herein may further comprise a pharmaceutically acceptable diluent or carrier suitable for topical use. The composition described herein may further comprise another agent.

Non-limiting examples of topical compositions include creams, lotions, gels, oils, ointments, solutions, sprays, foams, liniments, aerosols and transdermal devices for absorption through the skin.

Combinations with Other Agents

In accordance with one embodiment, the method, or composition described herein may include additional agents such as moisturizers, oils, fats, waxes, surfactants, thickening agents, antioxidants, viscosity stabilizers, chelating agents, buffers, preservatives, perfumes, dyestuffs, lower alkanols, humectants, emollients, dispersants, sunscreens such as radiation blocking compounds or particularly UV-blockers, antibacterials, antifungals, disinfectants, vitamins, or antibiotics, as well as other suitable materials that do not have a significant adverse effect on the activity of the salts or co-crystals.

Additional non-limiting examples of agents include for example cyclooxygenase inhibitors and non-steroidal anti-inflammatory drugs (NSAIDs) such as acetyl salicylic acid, ibuprofen and naproxen, peripheral analgesic agents, and narcotic analgesics. Non-limiting examples of additional analgesics include capsaicin, lidocaine, bupivacaine, mepivacaine, ropivacaine, tetracaine, etidocaine, chloroprocaine, prilocaine, procaine, benzocaine, dibucaine, dyclonine hydrochloride, pramoxine hydrochloride and proparacaine. Other agents employed for the treatment of neuropathic pain which may be used in the methods and compositions of the invention include ketamine (an NMDA receptor antagonist), amitriptyline (a tricyclic antidepressant), gabapentin or pregabalin (α2δ calcium channel agents) and guanethidine (a sympathetic blocking agent), in combination or independently.

EXAMPLES

The present invention will be more readily understood by referring to the following examples, which are provided to illustrate the invention and are not to be construed as limiting the scope thereof in any manner.

Chemical Synthesis of Salts

To synthesize clonidine, linsidomine and pentoxifylline salts/co-crystals, mechano-chemical reactions by neat, and/or liquid-assisted grinding (LAG) were performed using a Retsch MM400 shaker mill (Hann, Germany). One stainless steel ball (10 mm diameter, 4 g weight) in a 14-ml polytetrafluoroethylene (PTFE) jar was used and the milling conducted at 30 Hz for 30 minutes.

To synthesize clonidine and pentoxifylline salts/co-crystals, each of clonidine and pentoxifylline were mixed with equimolar quantities of α-lipoic acid, caffeic acid, gallic acid or protocatechuic acid. Clonidine was first purified from clonidine HCl (see below). The mechano-chemical reactions were run both neat (without solvent) and with small volumes of ethanol or nitromethane (50-100 μl) used as the liquid-assisted grinding (LAG) liquid additives. Linsidomine caffeate salt was synthesized by an anion exchange reaction. Caffeic acid was first reacted with equimolar quantities of sodium hydroxide (neat grinding, stainless steel jar, two stainless steel balls of 1.3 grams weight, at a shaking frequency of 30 Hz, and a milling time of 30 min). The product, validated to be sodium caffeate, was then milled with linsidomine chloride (LAG with 10 μl ethanol, PTFE jar, one 10 mm PTFE-covered ball, at a shaking frequency of 30 Hz, and a milling time of 45 min) to yield in linsidomine caffeate and sodium chloride.

Experiments for Validation and Characterization of Synthesized Salts

Fourier-Transform Infrared Spectroscopy

Different chemical functional groups in a molecule, depending on the chemical bonding and environment, absorb infrared light at varying frequencies. In an infrared (IR) spectrum, the percent absorbance/transmittance of a sample for IR radiation (light) of different frequencies can be used for chemical structure analysis and fingerprinting. Fourier-Transform Infrared Attenuated Total Reflectance (FTIR-ATR) measurements were performed on a Spectrum TWO FTIR with single bounce diamond ATR from Perkin Elmer.

Powder X-ray Diffraction (PXRD)

PXRD is a rapid analytical technique for identification of crystalline materials. It provides information on the unit cell dimension and atomic arrangement in a crystal. The measurement is done by performing an X-ray diffraction experiment using X-rays, and the results usually depicted in the form of maxima of X-ray diffraction with respect to the 2θ angle between the incident and diffracted beams. For a given X-ray wavelength, different crystalline solids will produce unique PXRD patterns that can serve as their identifying fingerprint. PXRD experiments on reaction products were conducted using a flat-plate mode on a Bruker D2 phaser equipped with nickel-filtered CuKα X-ray radiation.

Thermogravimetric Analysis (TGA)

TGA was performed using TGA Q500 (TA Instruments). Approximately 5 mg of sample was used for each experiment. Samples were heated over a temperature range of 25° C. to 600° C. The samples were purged with a flow of air and nitrogen throughout the experiment.

Drugs

Pentoxifylline, gallic acid and caffeic acid were obtained from Sigma-Aldrich, St. Louis, Mo. Linsidomine chloride, clonidine hydrochloride and protocatechuic acid were purchased from Cayman Chemicals, MI and α-lipoic acid from TCI chemicals, OR.

Formulation of Drugs into Topical Ointments

Topical drugs were formulated into ointment-type preparation using a composite, water-soluble polyethylene glycol base system consisting of 40% carbowax (PEG 3350) and 60% PEG 400 (both from Sigma Aldrich). The required amounts of the active ingredients were first weighted out and then added to the already molten base and mixed well. The vehicle treatment consisted of the same water-miscible base ointment without the addition of the active drugs.

Generation of the CPIP Rat Model of CRPS

The Chronic Post-ischemic Pain (CPIP) rat model of CRPS was prepared by inducing prolonged hind paw ischemia and subsequent reperfusion, as previously described by Coderre et. al., *Pain,* 112(1):94-105, 2004. In short, male Long Evans rats (300-400 g; Charles River, QC, Canada) were anesthetized over a 3-hour period with a bolus (55 mg/kg, intraperitoneally [i.p.]) followed by chronic i.p. infusion (0.15 mL/hour) of sodium pentobarbital (Ceva Sante Animale, Libourne, France) for 2 hours. Following induction of anesthesia, a Nitrile 70 Durometer O-ring (O-rings West, Seattle, Wash.) with an internal diameter of 5.5-mm was slipped around the rat's left hind limb proximal to the ankle joint to effect a complete blockade of arterial blood flow (Laferriere et al., *Mol Pain,* 4:49, 2008).

The ring was left in place for 3 hours, and the rats recovered from anesthesia 30 to 60 minutes following reperfusion.

Mechanical Sensitivity Testing As a measure of mechanical sensitivity, paw withdrawal threshold (PWT), was tested on plantar surface of the ipsilateral hind paw of the CPIP rats. The rats were first habituated for 30 minutes in the testing chambers. Nylon monofilaments (von Frey hairs) with thickness designed to apply stimulus intensity ranging between 1 g and 15 g were applied to the plantar surface of the rats' hind-paw. The filaments were applied for 10 seconds or until flexion reflex occurred. PWTs were determined using Chaplan's up and down method after testing with the filaments in either ascending (after negative response) or descending (after positive response) order to find the correct response pattern which was later matched with its corresponding 50% threshold of paw withdrawal (Chaplan et al., *J Neurosci Methods,* 53:55-63, 1994).

Statistics on Animal Behavioural Data

Time course measurements of PWTs after vehicle and drug administration were subjected to a repeated measure analysis of variance (ANOVA). Pairwise comparison was performed between PWTs obtained from drug and vehicle treatment groups measured at matching post-treatment times using Tukey's HSD test.

Cumulative anti-allodynic effect measured over 180-minute time course experiments was assessed by calculating the area under the curve (AUC) of PWT elevations plotted post-topical application. Comparisons of different drug doses versus vehicle were performed using repeated measure ANOVA followed by Tukey's HSD test.

Dose response curves for comparison of anti-allodynic potency were plotted on a semi-log scale with the amount of drug used per application on the X-axis and the AUC of the 180-minute PWT measured or change in PWT obtained post-drug application on the Y-axis. The linear regression of the dose-response curves was then calculated, and their difference analysed using a 1-way ANOVA.

Co-crystals of Pentoxifylline

To co-crystalize pentoxifylline with protocatechuic acid, caffeic acid, gallic acid and α-lipoic acid, both neat grinding and LAG reactions were performed at a 1:1 molar ratio of the two components. Pentoxifylline did not react with any of the acids following neat grinding. On the other hand, the addition of small volumes (50-100 μl) of ethanol to the grinding experiment facilitated the reaction and led to the formation of co-crystals of pentoxifylline and protocatechuic, caffeic and gallic acids (FIG. 1). Pentoxifylline and α-lipoic acid failed to react despite the varying reaction conditions attempted.

Salts of Clonidine

Figure 2:
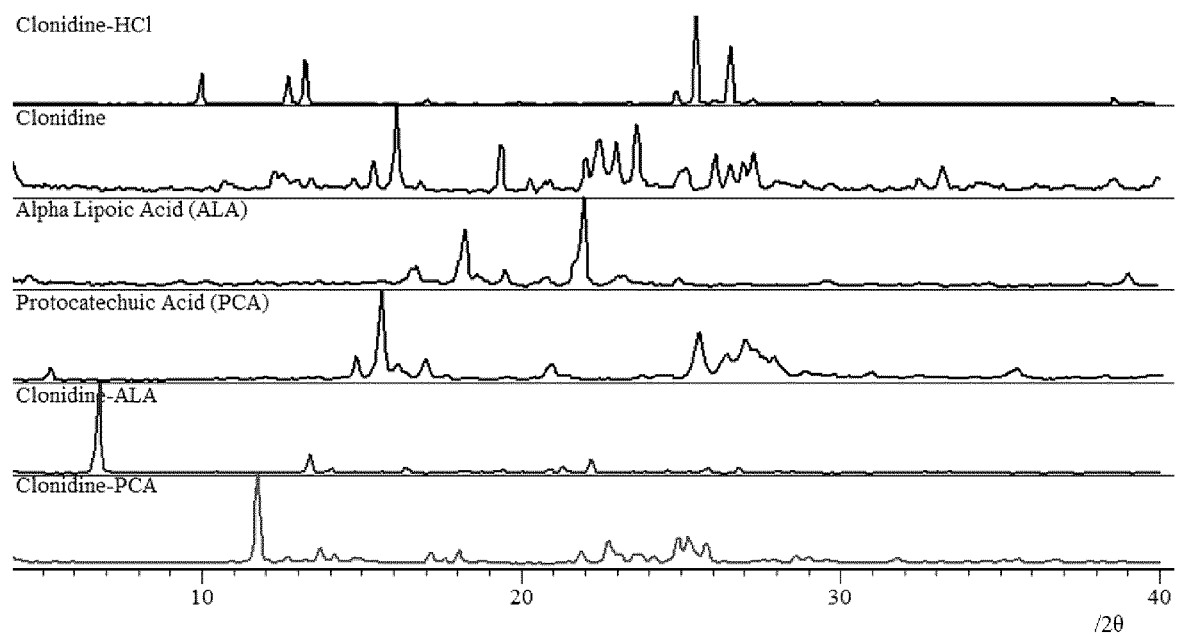
FIG. 2 is PXRD traces of clonidine, clonidine hydrochloride (HCl), certain acids (α-lipoic acid (ALA), protocatechuic (PCA)) and various salts obtained after liquid-assisted grinding (LAG)

The hydrochloride salt of clonidine was converted to its base form via a neutralization reaction with concentrated potassium hydroxide. After confirming the purity and chemical integrity of the pure base form using different spectroscopic techniques, LAG with ethanol of clonidine with α-lipoic, caffeic and protocatechuic acids was performed in a 1:1 molar ratio. The PXRD traces the LAG reactions of clonidine with α-lipoic and protocatechuic acid suggested the formation of a salt (FIG. 2). On the other hand, a similar LAG of clonidine with caffeic acid yielded products with a PXRD trace containing Bragg reflections of the starting materials, implying incomplete and/or inefficient compounding of the drugs.

Linsidomine and Caffeic Acid

Figure 3:
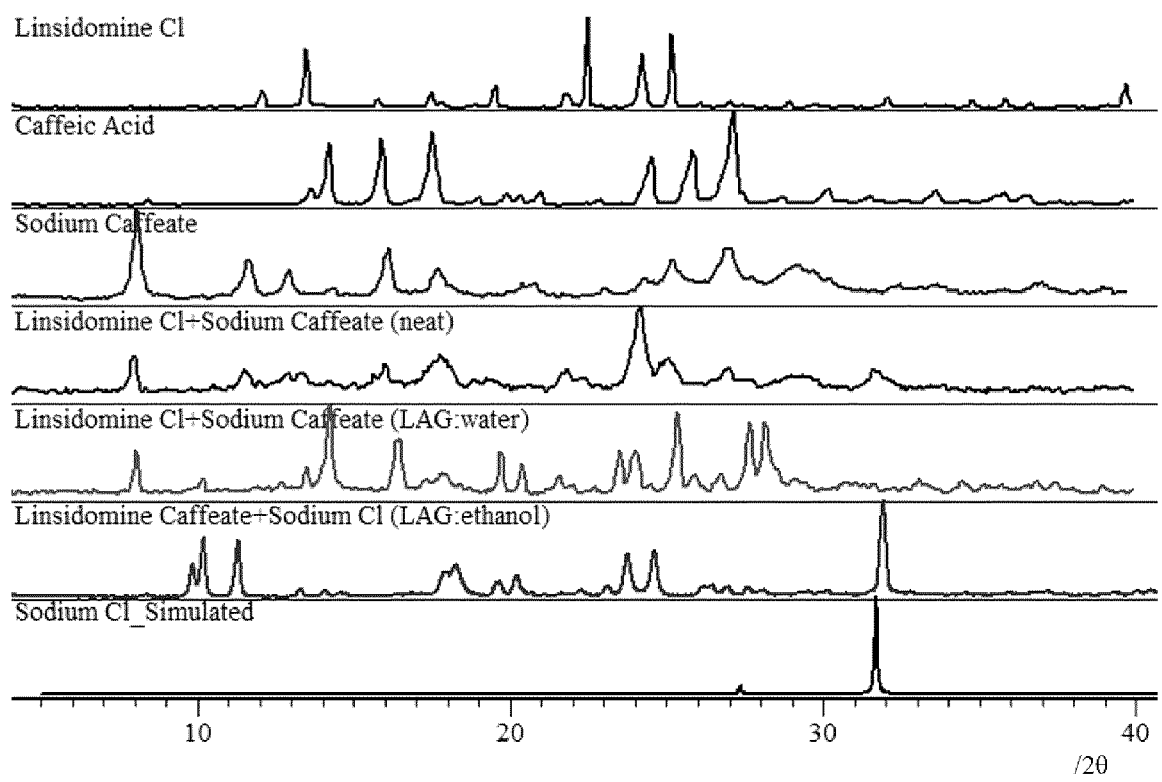
FIG. 3 is PXRD traces of linsidomine chloride (CO, caffeic acid, sodium caffeate and a salt obtained after neat and liquid-assisted grinding (LAG)

The reaction of linsidomine chloride and caffeic acid was designed to maximize their reactivity while maintaining linsidomine's stability, by using an anion exchange reaction whereby the chloride anion in linsidomine chloride was to be replaced with a caffeate anion yielding in the formation of linsidomine caffeate and sodium chloride. As a first step, a sodium salt of caffeic acid was prepared by the neat grinding of sodium hydroxide with caffeic acid. Reactions of linsidomine chloride with sodium caffeate were performed via neat grinding and LAG using ethanol and water (FIG. 3). The LAG with ethanol yielded linsidomine caffeate. The successful exchange of anions and formation of linsidomine caffeate could be ascertained by the presence of a distinct PXRD peak (at 2θ=31.7°) in the product mixture that belongs to sodium chloride (FIG. 3).

Infrared Spectroscopy

Analysis by FTIR spectroscopy was performed on the salts and co-crystals of clonidine, pentoxifylline and linsidomine to validate what has been observed with PXRD, and further characterize the products obtained. Although the spectra are not appended to this specification, absorption bands from both starting materials were seen in all spectra, indicating presence of both species in the products. Significant shifts were observed for the peaks corresponding to the starting materials is consistent with the formation of a co-crystal or salt.

For pentoxifylline-gallic acid, the absorption band at 1262 cm$^{-1}$ of the carboxylic acid moiety in gallic acid shifted to 1290 cm$^{-1}$, due to the O—H—N hydrogen bond, consistent with co-crystal formation. In the pentoxifylline-caffeic acid compound the absorption band at 1216 cm$^{-1}$ of the carboxylic acid moiety in caffeic acid shifted to 1236 cm$^{-1}$ due to the O—H—N hydrogen bond, also consistent with co-crystal formation. Similarly, the pentoxifylline protocatechuic acid compound showed an absorption band at 1438 cm$^{-1}$ consistent with a carboxylate or a salt, but the broad absorption band at 3217 cm$^{-1}$ indicative of an N—H group, implied the formation of a co-crystal.

For clonidine α-lipoic acid (clonidine-ALA), the absorption band at 1694 cm$^{1}$ of the carboxylic acid moiety in α-lipoic acid shifted to 1666 cm$^{-1}$ due to the O—H—N hydrogen bond, consistent with salt formation. The clonidine protocatechuic acid (clonidine-PCA) compound showed an absorption band at 1376 cm$^{-1}$ not found in the spectra of either of the starting materials, consistent with a carboxylate and implying the formation of a salt.

For linsidomine caffeate, the appearance of an absorption band at 1363 cm$^{-1}$, not found in the spectra of either of the starting materials, is consistent with a carboxylate, implying the formation of a salt.

Thermogravimetric Analysis (TGA)

TGA was also performed on the salts of clonidine, linsidomine and pentoxifylline with the aim of gaining insight into the components of the products synthesized, more specifically to discover if any of the co-crystals/salts synthesized are solvated, i.e. have some molecules of the LAG liquid additive (ethanol) incorporated into their structure.

Figure 4A:
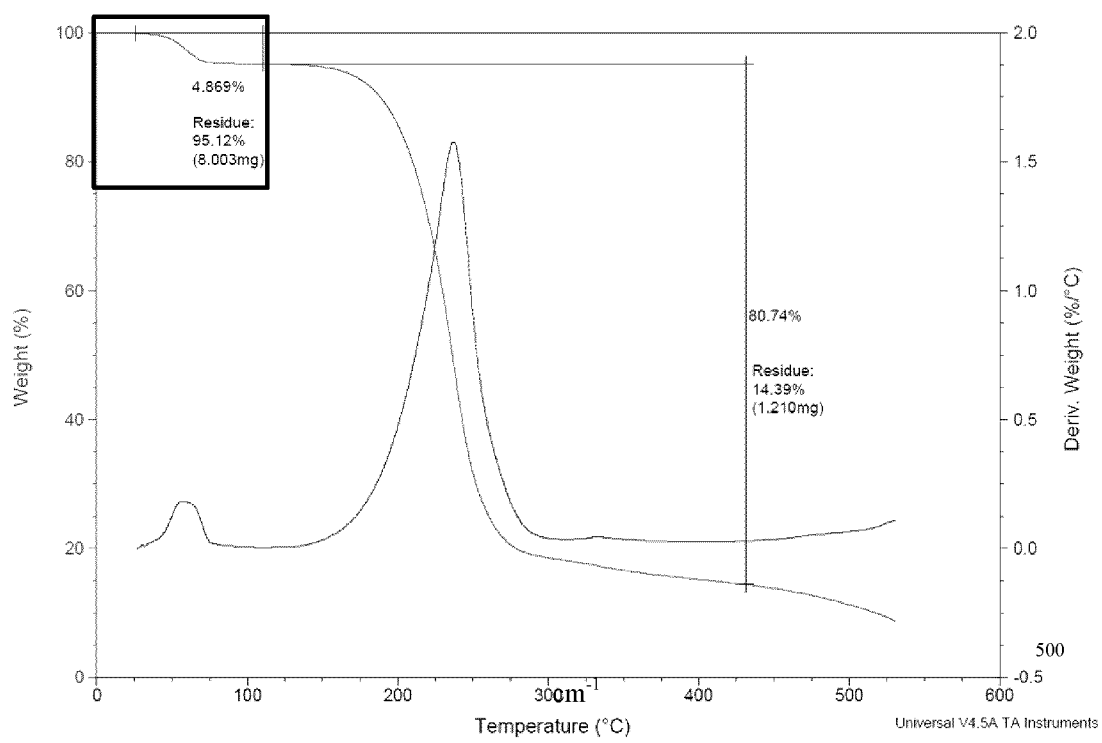
FIG. 4 (A-C) is the TGA of the clonidine α-lipoic acid (clonidine-ALA) salt and its starting materials.
Figure 4B:
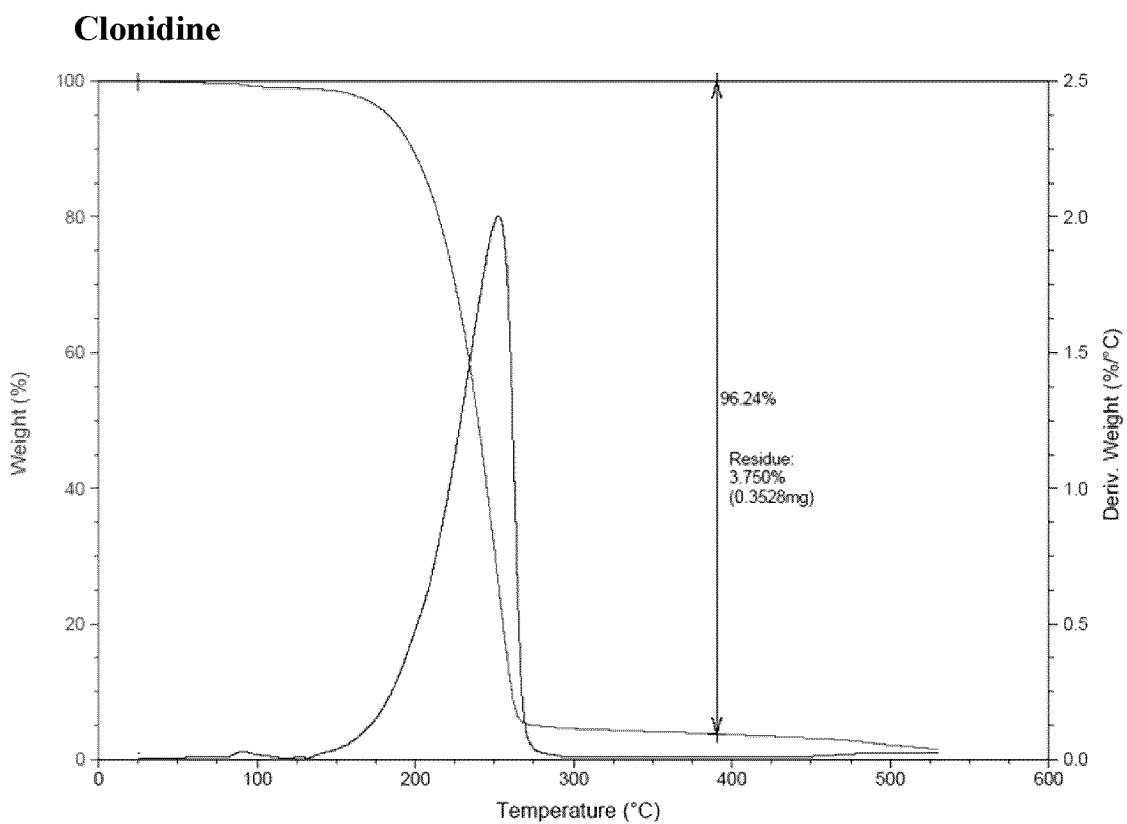
Figure 4C:
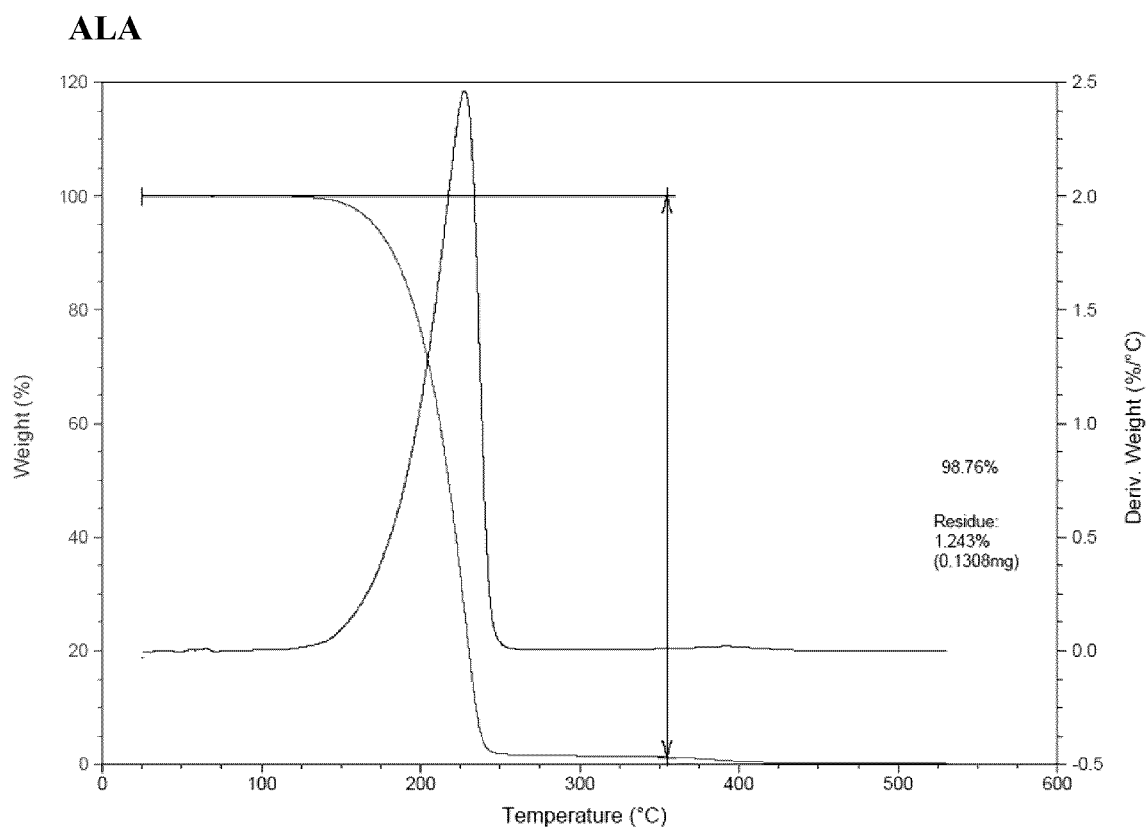

TGA of the clonidine α-lipoic acid (clonidine-ALA) salt and its starting materials was conducted and it was observed that clonidine-ALA appears to be a solvate of ethanol (FIG. 4A-C). This is implied by a 5% decrease weight of the sample in the early phases of the TGA heating cycle at a temperature range of 50-75° C. that corresponded to the boiling point of ethanol (FIG. 4A). The proportion of weight lost by the sample imply that there is 1 molecule of ethanol per 2 formula units of clonidine-ALA. This was not observed in either of the starting materials.

Solid-State NMR

Solid-state NMR (ssNMR) was performed using a Varian 400 MHz VNMRS wide bore spectrometer operating at a $^{1}$H frequency of 399.76 MHz, a $^{13}$C frequency of 100.53 MHz and a $^{15}$N frequency of 40.51 MHz. Cross-polarization magic angle spinning (CPMAS) $^{13}$C spectra were acquired using a 4 mm double-resonance probe while $^{15}$N CPMAS spectra were acquired using a 7.5 mm double-resonance probe. The spectra of sodium caffeate and linsidomine hydrochloride were acquired under spinning at 5 kHz while that of linsidomine caffeate was acquired at 8 kHz. The spectrum of linsidomine hydrochloride was compared with a cross-polarization total sideband suppression (CPTOSS) spectrum (not shown) to identify spinning sidebands. Total sideband suppression (TOSS) was used for the linsidomine hydrochloride spectrum. SPINAL-64 $^{1}$H decoupling was performed at 90 kHz. A recycle delay of 5 s was used for sodium caffeate and linsidomine hydrochloride and 6 s for linsidomine caffeate. Contact times of 3.5 ms, 1.5 ms, and 3.0 ms were used for sodium caffeate, linsidomine hydrochloride, and linsidomine caffeate, respectively. 128 transients were acquired of sodium caffeate, 1280 of linsidomine hydrochloride, and 172 of linsidomine caffeate. Samples were referenced to the carbonyl signal of glycine at 176.04 ppm. Both pentoxifylline and the pentoxifylline protocatechuic acid co-crystal were acquired under spinning at 5 kHz using a recycle delay of 20 s and contact time of 4 ms. 2560 scans were acquired of pentoxifylline and 1024 scans were acquired of the co-crystal.

$^{13}$C ssNMR of Linsidomine Caffeate

Figure 10A:
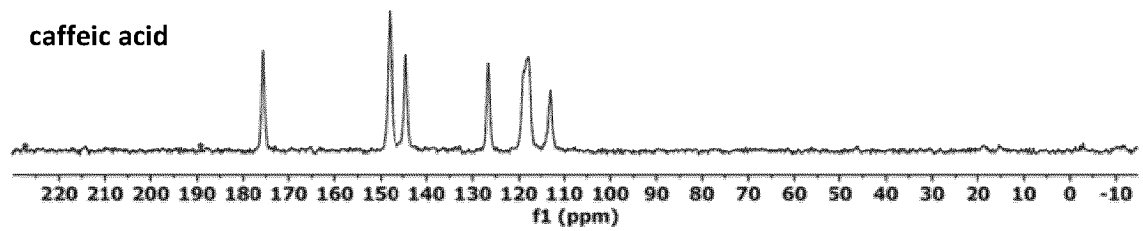
FIG. 10A is $^{13}$C solid-state NMR spectra of caffeic acid (Spinning side bands indicated by *)
Figure 10B:
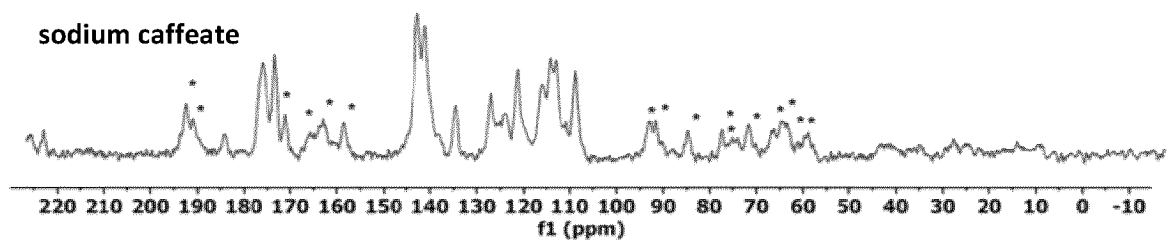
FIG. 10B is $^{13}$C solid-state NMR spectra of sodium caffeate (Spinning side bands indicated by *)
Figure 10C:
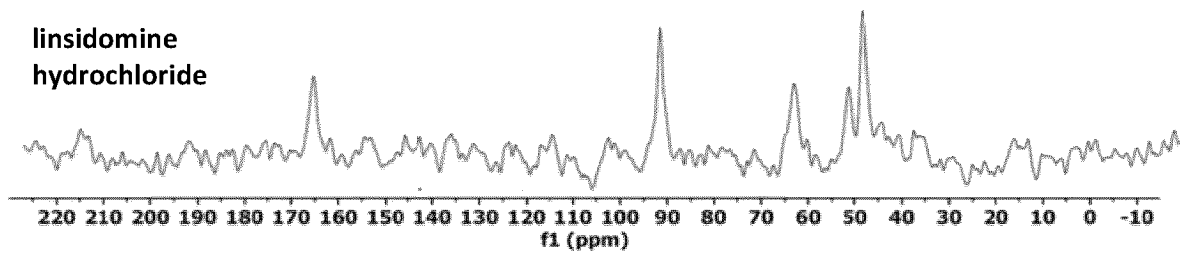
FIG. 10C is $^{13}$C solid-state NMR spectra of linsidomine hydrochloride (Spinning side bands indicated by *)
Figure 10D:
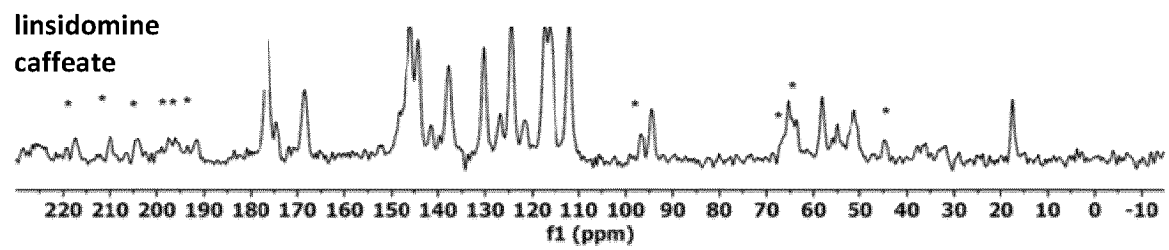
FIG. 10D is $^{13}$C solid-state NMR spectra of linsidomine caffeate (Spinning side bands indicated by *)

Upon examination with ssNMR, sodium caffeate contained at least two signals at 176.3 and 179.0 ppm for the carboxylate $^{13}$C, suggesting that Z'≥2 (the number of molecules in the asymmetric unit is at least 2) (FIG. 10B). Linsidomine hydrochloride had all its signals present and Z'=1. Its signals are presumably overlapped at 52.3 ppm (FIG. 10C). Linsidomine caffeate appeared to have a set of intense and a set of less intense signals. Perhaps Z'=3 or Z'=4, so that some signals are present in a 2:1 or 3:1 ratio (FIG. 10D). Compared with the spectrum of sodium caffeate, changes in chemical shift are noticeable at the carboxylate peaks (sodium caffeate: 179.3 and 176.5 ppm; linsidomine caffeate: 176.5 and 174.4 ppm) and there is some change at the C—OH signals (appearance of signal at 174.4 ppm—assignment done using non-quaternary carbon suppression experiment) (FIG. 10). The signal at 119.2 ppm in the sodium caffeate spectrum has shifted to 121.6 ppm in the linsidomine caffeate spectrum, but it is not certain what signal that peak corresponds to. There are not many changes between the linsidomine hydrochloride and the linsidomine caffeate spectrum—the largest is from 66.7 ppm (linsidomine hydrochloride) to 65.3 ppm (linsidomine caffeate) at the signal from the aliphatic C—O carbons (assigned on the basis of expected chemical shift).

The appearance of the carboxylate peak of linsidomine caffeate and sodium caffeate closely downfield from the neutral carboxylic acid carbon peak of caffeic acid (FIG. 10A) at 175 ppm is good evidence that both compounds contain a deprotonated caffeate anion (FIG. 10). With the minimal changes seen between the spectra of linsidomine hydrochloride and linsidomine caffeate, the composition of the linsidomine caffeate product is most likely that of a salt between a protonated linsidomine and a caffeate anion.

$^{15}$N ssNMR Pentoxifylline Protocatechuic Acid

Figure 11A:
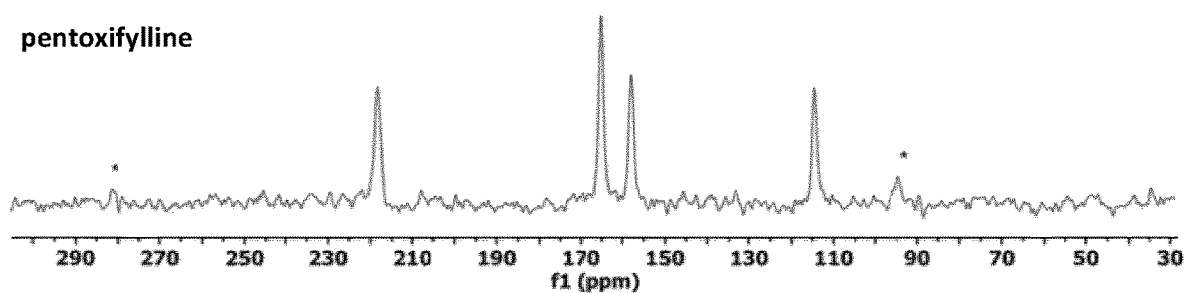
FIG. 11A is $^{15}$N solid-state NMR spectra of pentoxifylline (Spinning side bands indicated by *)
Figure 11B:
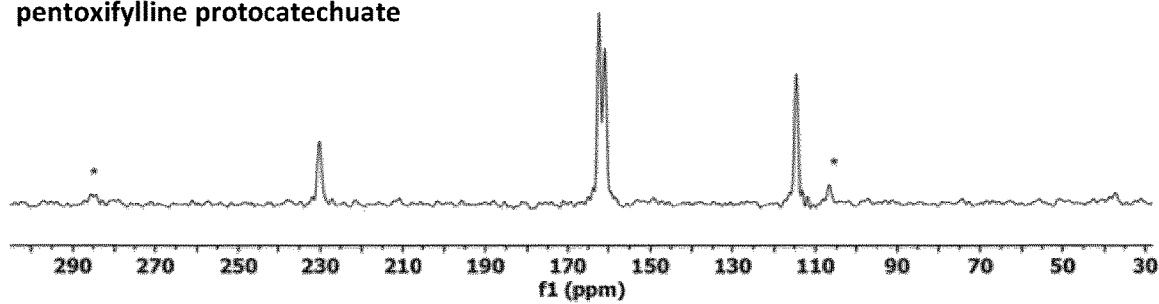
FIG. 11B is $^{15}$N solid-state NMR spectra of pentoxifylline protocatechuic acid co-crystal (Spinning side bands indicated by *)

The largest chemical shift change between pentoxifylline (FIG. 11A) and the pentoxifylline protocatechuic acid (FIG. 11B) co-crystal was observed at the C=N site at position 1 of the imidazole ring, which is the site in pentoxifylline that interacts most strongly with the protocatechuic acid.

Assessment of the Anti-allodynic Effects of Salts/Co-crystals of Pentoxifylline, Clonidine and Linsidomine on CRPS The synthesized salts/co-crystals of pentoxifylline, clonidine and pentoxifylline were formulated into a polyethylene based topical ointment and their analgesic efficacy and potency tested and compared to their parent drugs on the CPIP rat model of CRPS.

The Anti-allodynic Effects of Topical Pentoxifylline Protocatechuic Acid

Figure 5A:
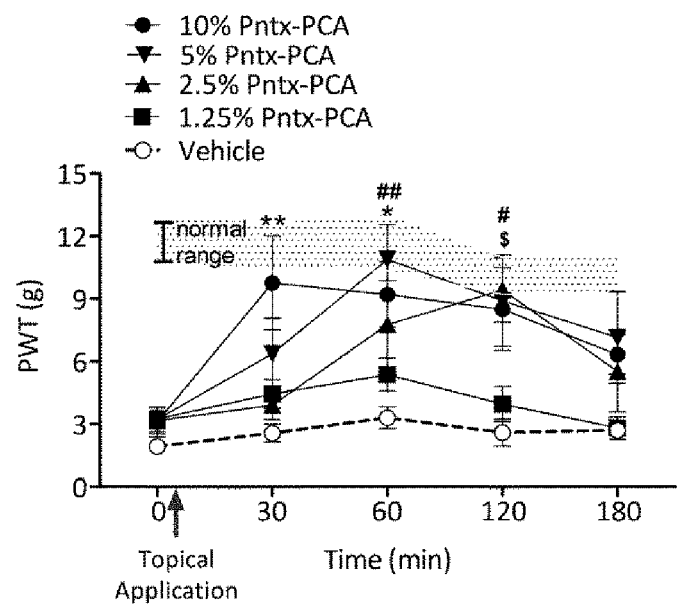
FIG. 5 (A-D) are graphs representing the topical anti-allodynic effects of pentoxifylline protocatechuic acid (Pntx-PCA) in CRPS rats.
Figure 5B:
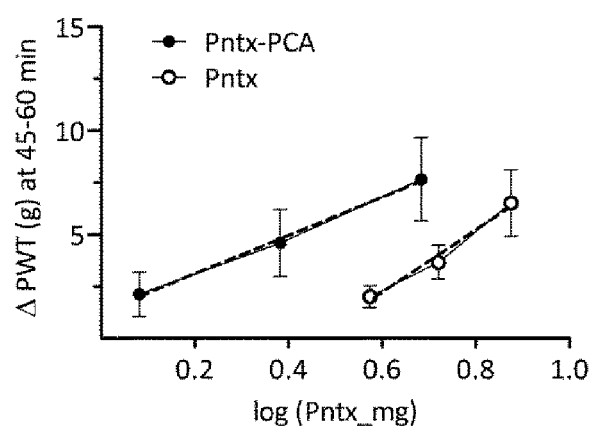
Figure 5C:
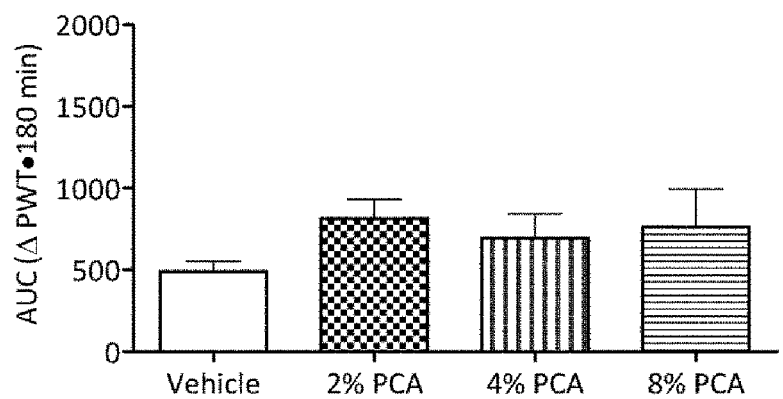
Figure 5D:
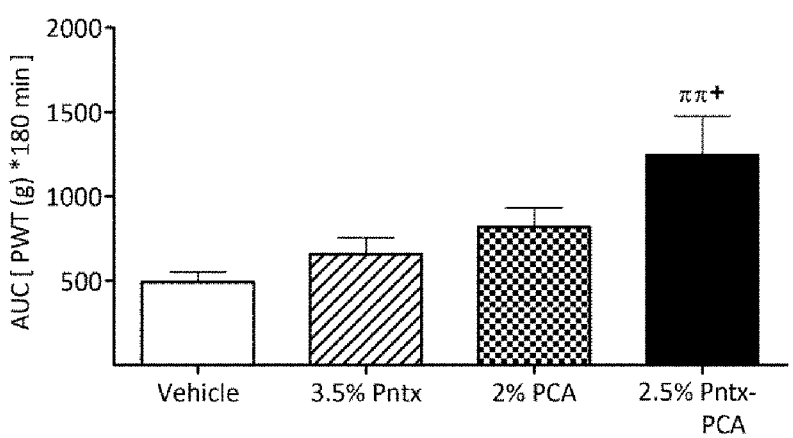

FIG. 5A represents the time course of paw withdrawal threshold (PWT) response profile to topical application of different concentrations of pentoxifylline-protocatechuic acid (Pntx-PCA), the shaded area represents PWT values from vehicle-treated normal animals). ($^{*,\#,\$}$ p<0.05 $^{**, \#\#}$p<0.01, W/W 10% (*), 5% ($^{\#}$) and 2.5% ($^{\$}$) Pntx-PCA compared to corresponding vehicle PWT, n=8). The topical application of the Pntx-PCA salt on the ipsilateral hind paw of CRPS rats produced significant anti-allodynic effects 30 to 60-minutes post-application at doses 5 and 10% W/W compared to application of ointment base alone (FIG. 5A). Co-crystallization with PCA results in a significant leftward shift of the log-dose response curve of Pntx by 0.59 log units (p=0.0113) (FIG. 5B). This shift translates to a close to 4-fold increase in potency. Moreover, the cumulative 3-hour anti-allodynic effect of the lowest effective dose of Pntx-PCA (2.5%, constituted of 1.5% Pntx and 1% PCA W/W) significantly exceeds the effect achieved by double the amount of its constituent drugs (3.5% Pntx and 2% PCA W/W) ($^{\pi\pi}$p<0.01 as compared to 3.5% Pntx, $^{+}$p<0.05 as compared to 2% PCA) (FIG. 5D). PCA, topically applied at the different w/w doses contained in the Pntx-PCA co-crystal, does not produce significant anti-allodynic effects as compared to vehicle (FIG. 5C).

The Anti-allodynic Effects of Topical Pentoxifylline Caffeic Acid

Figure 6A:
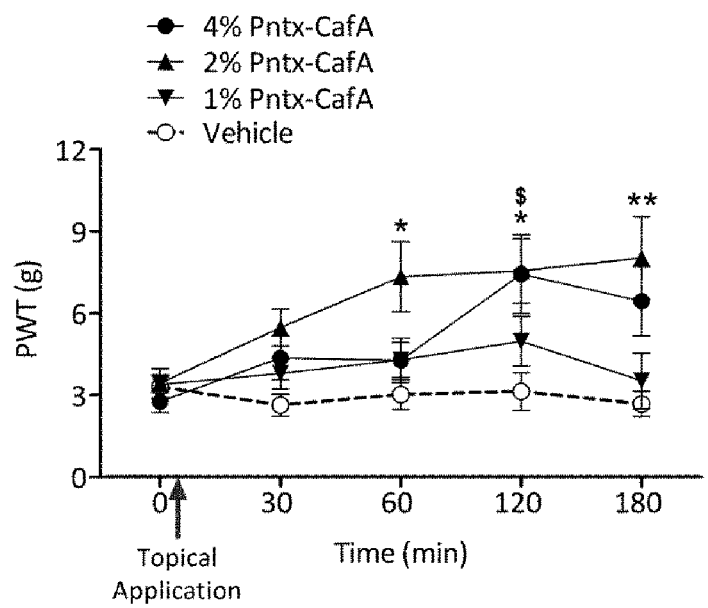
FIG. 6 (A-C) are graphs representing the topical anti-allodynic effects of pentoxifylline caffeic acid (Pntx-CafA)
Figure 6B:
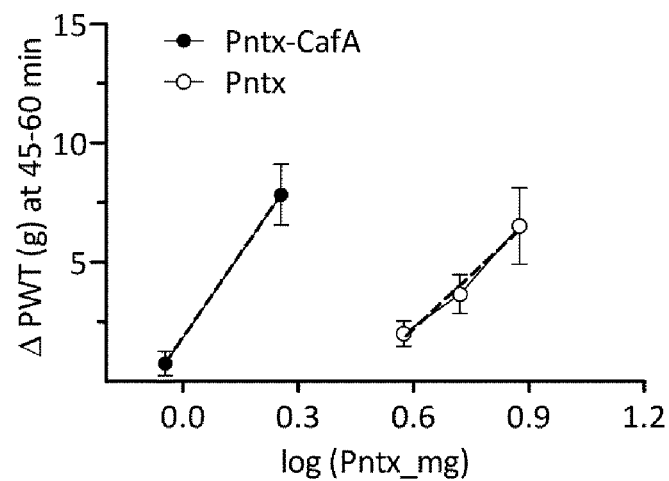
Figure 6C:
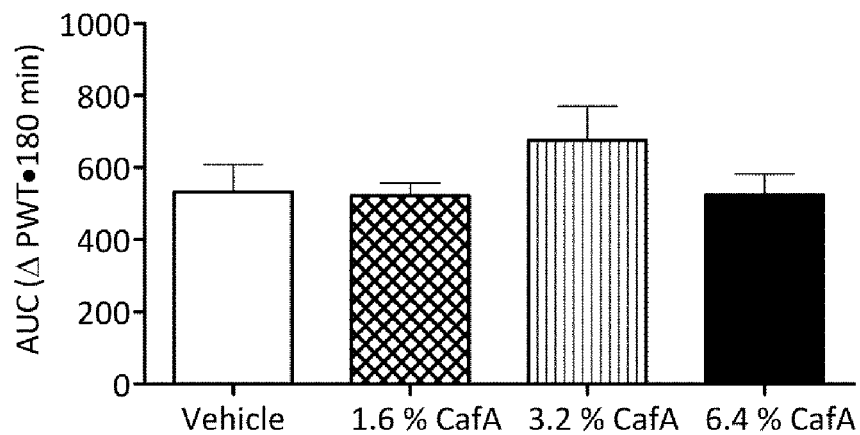

FIG. 6A represents the time course of paw withdrawal threshold (PWT) response profile to topical application of different concentrations of pentoxifylline-caffeic acid (Pntx-CafA) salt. Pntx-CafA produced significant and sustained elevation of PWTs at a low concentration of 2% W/W compared to vehicle at 60, 120 and 180 minutes post application (p=0.04, p=0.03 and p=0.0024 respectively) (FIG. 6A; n=10). This effect did not improve with a higher dose of 4% W/W. However, the co-crystal was seen to have a more potent anti-allodynic effect in the linear segment of its dose-response curve made up by the two concentrations of Pntx-CafA (2% W/W and 1% W/W) when compared to that of Pntx alone (FIG. 6B). Three different concentrations of CafA alone, in amounts that correspond to W/W levels contained in the Pntx-CafA co-crystal produced no anti-allodynic effect upon topical application (FIG. 6C; n=10).

The Effect of Topical Pentoxifylline Gallic Acid

Figure 7A:
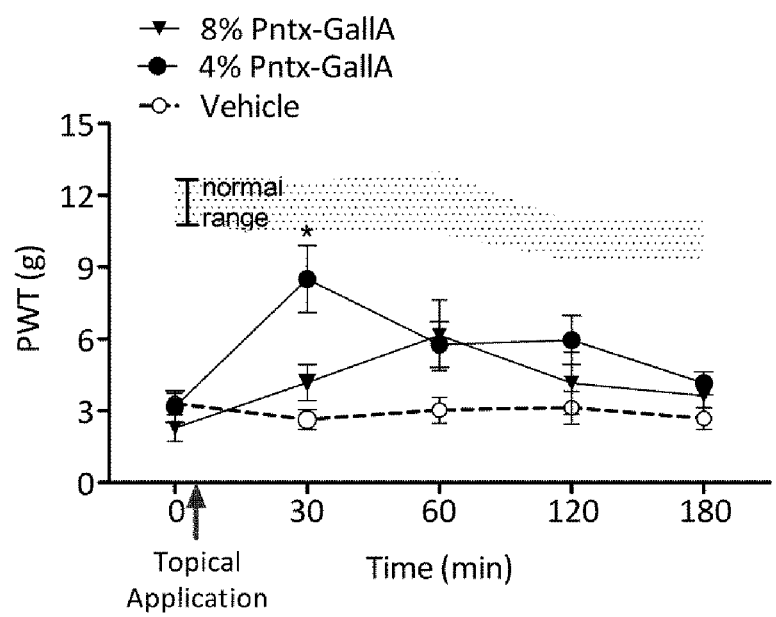
FIG. 7 (A-B) are graphs representing the topical anti-allodynic effects of pentoxifylline gallic acid (Pntx-GallA) in CRPS rats.
Figure 7B:
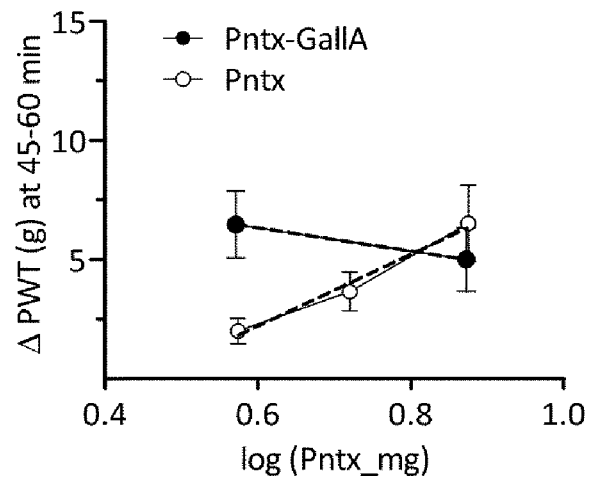

FIG. 7A represents the anti-allodynic effects of the pentoxifylline-gallic acid (Pntx-GallA) co-crystal in CRPS rats wherein the shaded area represents PWT values from vehicle-treated normal animals. Topical formulations of the GallA salt of Pntx produced modest anti-allodynic effects in the CRPS rats. The significant improvement in PWT was observed at the only dose of 4% W/W ($^{*}$p<0.05 compared to the corresponding vehicle PWT) (FIG. 7A). Moreover, there was no significant measurable difference in the change in PWT attained upon topical application of different doses of the co-crystal versus respective doses of Pntx during the 3 hours of testing following topical application (FIG. 7B).

The Anti-allodynic Effects of Clonidine α-Lipoic Acid

Figure 8A:
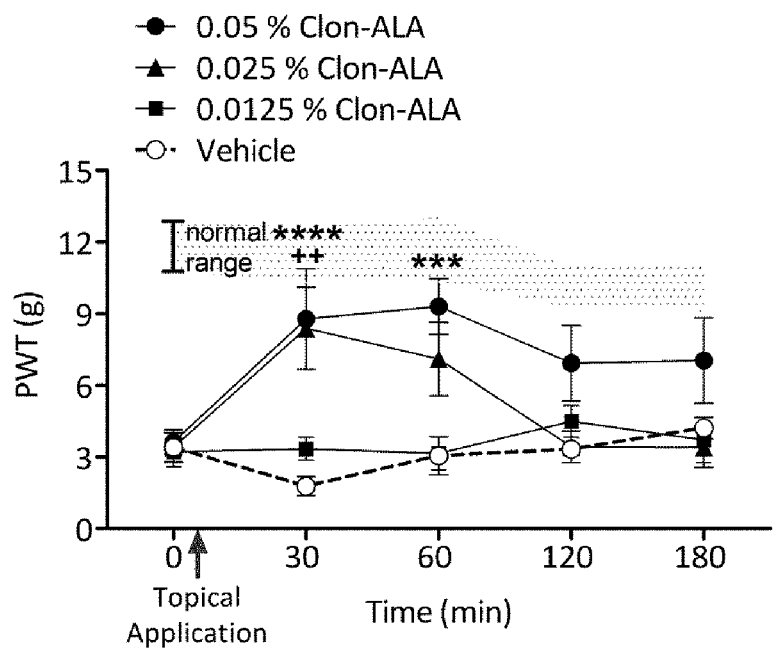
FIG. 8 (A-B) are graphs representing the topical anti-allodynic effects of clonidine α-lipoic acid (Clon-ALA) in CRPS rats.
Figure 8B:
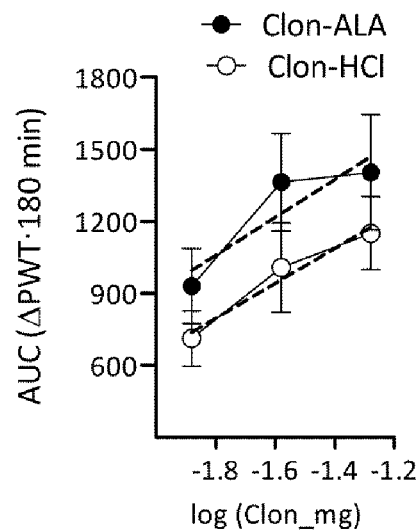

FIG. 8A represents the time course of change in PWTs after application of different doses of clonidine-α-lipoic acid (Clon-ALA) compared to the vehicle. Topical application of Clon-ALA, dose-dependently, relieves mechanical hypersensitivity in CRPS rats. A w/w concentration of 0.025% Clon-ALA brings about a significant rise in PWTs at 30 minutes post-application compared to vehicle, whereas at a dose of 0.05% the PWTs stay significantly higher for twice as long. The shaded area represents PWT values from vehicle-treated normal animals (++p<0.01, *p<0.001, **p<0.0001 W/W 0.025% (+), 0.05% (*), n=7 (FIG. 8A). The change in PWTs observed over a 3-hour time course of testing after topical application of Clon-ALA, as compared to Clon-HCl, shows a small but significant improvement in its anti-allodynic potency. The x-intercept of the dose response curve for Clon-ALA, as compared to Clon-HCl, is shifted significantly leftward by 0.265 log units (p=0.04), which converts to a nearly 2× increase in potency (FIG. 8B).

The Anti-allodynic Effects of Topical Linsidomine Caffeate

Figure 9A:
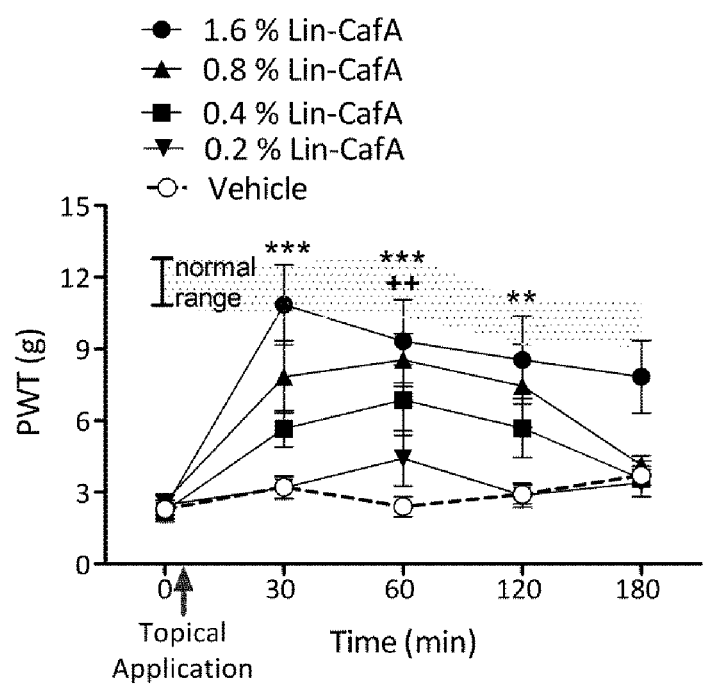
FIG. 9 (A-C) are graphs representing the topical anti-allodynic effects of linsidomine caffeic acid (Lin-CafA) in CRPS rats.
Figure 9B:
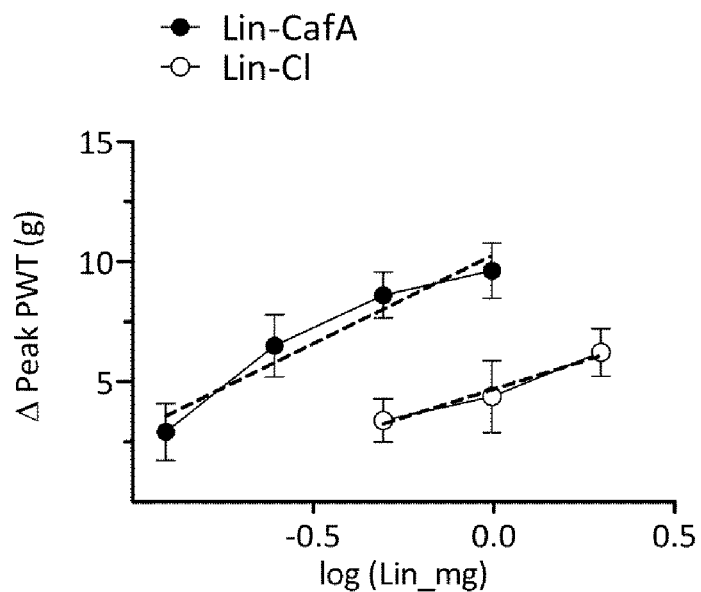
Figure 9C:
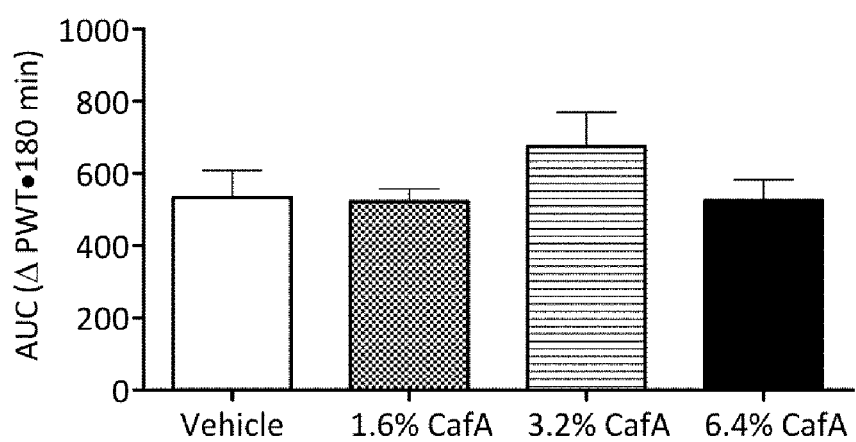

FIG. 9A represents the time course of change in PWTs after application of different doses of linsidomine-caffeate (Lin-CafA) compared to the vehicle. The topical application of linsidomine-caffeate (Lin-CafA) at W/W doses of 1.6% and 0.8% produces significant anti-allodynic effect on CRPS rats for as long as 120 minutes post-application (the shaded area represents PWT values from vehicle treated normal animals) (, ++p<0.01, *p<0.001 W/W 0.8% (+), 1.6% (*) n=9. At w/w concentrations of 1.6%, Lin-Caf significantly elevates PWTs to non-allodynic values at 30, 60 and 120 minutes post-application (p<0.0001, p=0.00013 and p=0.009 respectively) as compared to vehicle (FIG. 9A). This anti-allodynic effect is dose-dependent with each doubling of dose producing proportional rise in PWTs. A comparison of the dose response curve of Lin-CafA with linsidomine chloride shows the Lin-CafA salt to have greater efficacy and potency. The maximum change in PWTs obtained after topical application of the chloride salt is (6.23±0.99), but the Lin-CafA salt brings about greater rise in PWTs (9.6±1.15) despite having half of the linsidomine content. The x-intercept of the dose response curve for Lin-CafA is significantly shifted to the left by 0.3966 log units as compared to Lin-Cl (p=0.0026). This shift translates to a close to 2.5-fold increase in potency (FIG. 9B). Topical administration of CafA on its own exhibited no anti-allodynic effects (FIG. 9C).

Potential Systemic Effect After Topical Treatment

To assess for any contribution systemic absorption might have to the anti-allodynic effects seen with the novel salts and co-crystals, we performed a control experiment using contralateral topical administration of the compounds. A topical preparation of the salts and co-crystals at a concentration proven to produce anti-allodynia, was applied to the uninjured contralateral paw of the CRPS rats and the effect this had on the PWT of the injured CRPS paw was measured at 30, 60, 120 and 180 minutes post topical application. The PWT obtained at 30, 60, 120 and 180 minutes post topical application were then compared with the values obtained after direct topical application on the injured CPRS paw.

Figure 12A:
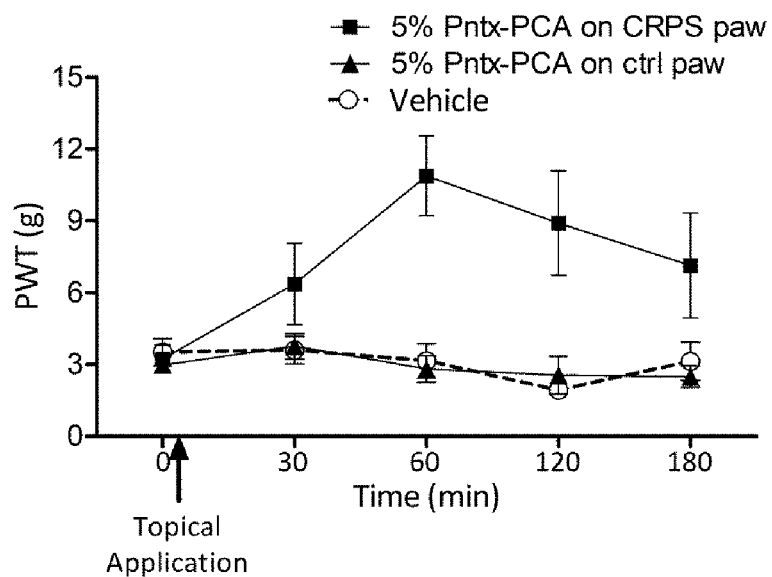
FIG. 12A is a graph representing an assessment of the contribution of systemic absorption to the anti-allodynic effects of pentoxifylline protocatechuic acid (Pntx-PCA in CRPS.
Figure 12B:
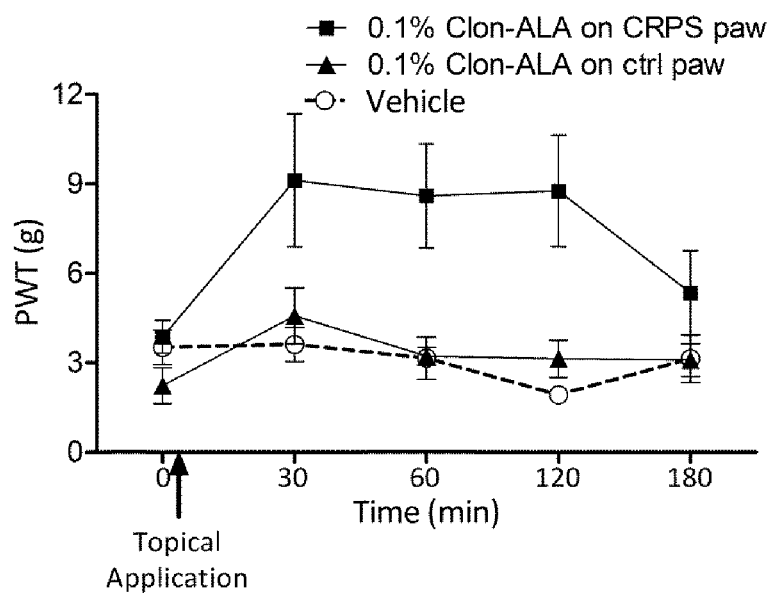
FIG. 12B is a graph representing an assessment of the contribution of systemic absorption to the anti-allodynic effects of clonidine α-lipoic acid (Clon-ALA) in CRPS rats.
Figure 12C:
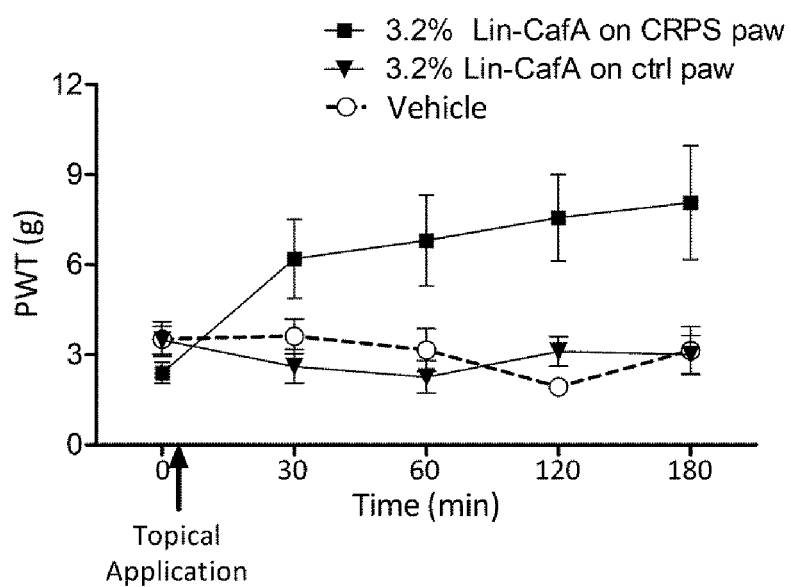
FIG. 12C is a graph representing an assessment of the contribution of systemic absorption to the anti-allodynic effects of linsidomine caffeate (Lin-CafA) in CRPS rats.

The topical application of pentoxifylline-protocatechuate, clonidine α-lipoate and linsidomine caffeate, at concentrations previously demonstrated to relieve allodynia when topical applied to the injured CRPS-paws, produced no anti-allodynic effects when applied to the contralateral (uninjured) paws of CRPS rats (FIG. 12 A-C). The PWTs measured after contralateral application lie at levels comparable to what is observed after topical administration of vehicle (FIG. 12 A-C). This indicates that post-topical application systemic absorption and distribution has no role in the anti-allodynic effects produced by the topical preparations of the salts/co-crystal.

The invention claimed is:

1. A compound salt/co-crystal selected from pentoxifylline caffeate, pentoxifylline protocatechuate, clonidine α-lipoate and linsidomine caffeate or a solvate thereof.

2. The compound of claim 1 which is pentoxifylline caffeate.

3. The compound of claim 1 which is pentoxifylline protocatechuate.

4. The compound of claim 1 which is clonidine α-lipoate.

5. The compound of claim 1 which is clonidine α-lipoate as an ethanol solvate.

6. The compound of claim 1 which is linsidomine caffeate.

7. A composition comprising a compound salt/co-crystal as defined in claim 1 and a pharmaceutically acceptable diluent or carrier.

8. A method for preventing or treating pain comprising topically administering an effective amount of a salt/co-crystal selected from pentoxifylline caffeate, pentoxifylline protocatechuate, clonidine α-lipoate and linsidomine caffeate or a solvate thereof to a subject in need thereof.

9. The method of claim 8 wherein said the pain is neuropathic, ischemic, muscle pain, pain associated with peripheral nerve injury induced by trauma, metabolic dysfunction, chemotherapy, viral or bacterial disease, nerve compression or neurologic conditions, or pain associated with angina, peripheral arterial disease, fibromyalgia, or conditions involving mixed inflammatory and neuropathic pain.

10. The method of claim 8 further comprising administering an effective amount of at least another agent useful for preventing or treating pain to a subject in need thereof.

11. The method of claim 10 wherein said another agent is administered concurrently or sequentially with the salt/co-crystal or a solvate thereof.

12. The method of claim 10, wherein said another agent is a cyclooxygenase inhibitor, a non-steroidal anti-inflammatory drugs (NSAIDs), a peripheral analgesic agent, a narcotic analgesic, an NMDA receptor antagonist, a tricyclic antidepressant, an α2δ calcium channel agent, or a sympathetic blocking agent, or a combination thereof.

13. A method for preparing pentoxifylline caffeate, pentoxifylline protocatechuate, clonidine α-lipoate or linsidomine caffeate salt/co-crystal or a solvate thereof, comprising liquid-assisted grinding of an equimolar quantities of pentoxifylline with caffeic acid, pentoxifylline with protocatechuic acid, clonidine with α-lipoic acid or a caffeate salt with a linsidomine salt.

14. The method of claim 13, wherein said grinding is conducted in a jar together with one or more grinding balls.

15. The method of claim 13, wherein said liquid is ethanol or nitromethane.

16. The method of claim 13 wherein said caffeate salt is sodium caffeate.

17. The method of claim 13 wherein said linsidomine salt is linsidomine chloride.

* * * * *